United States Patent [19]
Goedeke

[11] Patent Number: 6,167,312
[45] Date of Patent: Dec. 26, 2000

[54] TELEMETRY SYSTEM FOR IMPLANTABLE MEDICAL DEVICES

[75] Inventor: Steven D. Goedeke, Forest Lake, Minn.

[73] Assignee: Medtronic, Inc., Minneapolis, Minn.

[21] Appl. No.: 09/302,637

[22] Filed: Apr. 30, 1999

[51] Int. Cl.$^7$ .................................................. A61N 1/02
[52] U.S. Cl. .............................................. 607/60; 607/32
[58] Field of Search ..................... 607/32, 60; 128/703

[56] References Cited

U.S. PATENT DOCUMENTS

| | | |
|---|---|---|
| 4,365,290 | 12/1982 | Nelms et al. . |
| 4,523,324 | 6/1985 | Marshall . |
| 4,542,532 | 9/1985 | McQuilkin . |
| 4,543,953 | 10/1985 | Slocum et al. . |
| 4,580,101 | 4/1986 | Lax . |
| 4,618,967 | 10/1986 | Vance et al. . |
| 4,958,645 | 9/1990 | Cadell et al. . |
| 5,107,833 | 4/1992 | Barsness . |
| 5,113,869 | 5/1992 | Nappholz et al. . |
| 5,309,919 | 5/1994 | Snell et al. . |
| 5,336,245 | 8/1994 | Adams et al. ............................ 607/32 |
| 5,342,408 | 8/1994 | deCoriolis et al. . |
| 5,350,411 | 9/1994 | Ryan et al. . |
| 5,354,319 | 10/1994 | Wyborny et al. . |
| 5,383,915 | 1/1995 | Adams . |
| 5,404,877 | 4/1995 | Nolan et al. . |
| 5,476,488 | 12/1995 | Morgan et al. . |
| 5,480,415 | 1/1996 | Cox et al. . |
| 5,527,348 | 6/1996 | Winkler et al. . |
| 5,683,432 | 11/1997 | Goedeke et al. . |
| 5,693,076 | 12/1997 | Kaemmerer . |
| 5,697,958 | 12/1997 | Paul et al. . |
| 5,704,351 | 1/1998 | Mortara et al. . |
| 5,720,770 | 2/1998 | Nappholz et al. . |
| 5,752,976 | 5/1998 | Duffin et al. . |
| 5,752,977 | 5/1998 | Grevious et al. . |
| 5,759,199 | 6/1998 | Snell et al. . |
| 5,766,232 | 6/1998 | Grevious et al. . |
| 5,861,019 | 1/1999 | Sun et al. . |

OTHER PUBLICATIONS

U.S. patent application filed Apr. 30, 1999 by Villaseca et al. for a "Telemetry System for Implantable Medical Devices".

*Primary Examiner*—George R. Evanisko
*Attorney, Agent, or Firm*—Reed A. Duthler; Harold R. Patton; Girma Wolde-Michael

[57] ABSTRACT

A device for use in communication with an implantable medical device. The device is provided with a spatial diversity antenna array mounted to the device housing and an operating at defined frequency, located within the device housing, coupled to the antenna array. The antenna array includes at least one antenna permanently mounted to the device housing and an antenna removably mounted to the device housing and locatable at a distance from the housing, coupled to the RF transceiver. A device controller selects which of the antennas in the antenna array is coupled to the transceiver responsive to the quality of signals received by the antennas.

6 Claims, 6 Drawing Sheets

FIG. 7

TELEMETRY SYSTEM FOR IMPLANTABLE MEDICAL DEVICES

BACKGROUND OF THE INVENTION

This invention relates generally to implantable medical devices and more specifically to telemetry systems for allowing communication between implanted medical devices and external programmers or monitors.

In the context of implantable medical devices, it has become common to provide a communication link between the implanted device and an external programmer or monitor in order to allow for transmission of commands from the external device to the implanted device and to allow for transmission of stored information and/or sensed physiological parameters from the implanted device to the external programmer. Conventionally, communication between an implanted device and an external programmer has been accomplished by means of a telemetry system which includes a transceiver located within the implanted medical device and an external programmer or monitor, also having a transceiver and one or more antennas. The implanted device typically includes an antenna located either within the hermetic device housing containing the circuitry, as disclosed in U.S. Pat. No. 4,542,532 issued to McQuilkn, in a plastic header or connector block used to interconnect the device to electrical leads as disclosed in U.S. Pat. No. 5,697,958 issued to Patrick et al. or mounted to the device housing as in U.S. Pat. No. 5,861,019 issued to Sun et al. and U.S. Pat. No. 5,720,770 issued to Nappholz et al., all incorporated herein in their entireties. The programmer or monitor typically includes or consists of a programming head containing an antenna, intended to be placed on the patient's body in close proximity to the implanted device. The programming head may be coupled to the external programmer or monitor by means of a cord, as disclosed in U.S. Pat. No. 5.766,232 issued to Grevious et al.

More recently it has been proposed to provide communication systems for implantable devices in which the programming head is done away with, and communication occurs directly between the programmer or monitor, which may be located some distance from the patient, and the implanted medical device. Such systems are disclosed in U.S. Pat. No. 5,404,877 issued to Nolan et al, and U.S. Pat. No. 5,113,869 issued to Nappholz, both incorporated herein by reference in their entireties. In the Nappholz patent, in particular, the use of an electrical lead as the antenna for broadcasting RF signals to the programmer or monitor which may be located some feet away from the patient is suggested.

SUMMARY OF THE INVENTION

The present invention is directed toward a telemetry system for an implantable device which, like the devices in the above cited Nolan and Nappholz patents allows for communication between an implanted device and an associated external programmer or monitor without the necessity of a programming head placed on the patient's body in close proximity to the implanted device. In conjunction with this invention, improved antenna configurations for the programmer are provided, optimized to allow for reliable communication between an implanted device and an external programmer or monitor which may be spaced at least several feet from one another. In one preferred embodiment, the transceivers employed in the programmer or monitor and the implantable device take the form of RF transceivers operating at about 400 megaHertz.

A programmer or monitor according to the invention is provided with a spatial diversity antenna array in order to facilitate reception of signals from the implanted device and transmission of signals to the implanted device, within a wide area surrounding the monitor or programmer. The antenna array includes at least one antenna permanently and fixedly mounted to the housing of the monitor or programmer and an additional antenna removably mounted to the housing of the programmer or monitor and connected thereto by means of a cord or other mechanism which allows communication between the transceiver within the programmer or monitor and the removable antenna when they are spaced at least several feet from one another. The removably mounted antenna is normally employed while mounted to the housing, as part of the antenna array. However, in cases in which a robust telemetry link between the programmer or monitor and an associated implanted device is not possible with the programmer or monitor located at a distance from the patient, for example due to interference, the removably mounted antenna may be placed in close proximity to the patient and to the implanted device. The removable antenna may take the form of a tuned monopole.

The antenna of the implanted device may take the form of a monopole antenna located external to the hermetic enclosure of the implanted device, having a length tuned to function optimally at the radio frequencies chosen for use in the telemetry system, as generally disclosed in the above-cited Nappholz patent. In preferred embodiments, the antenna of the implantable device may take the form of any of the antennas described in commonly assigned, co-pending U.S. Patent Application filed on even date herewith by Dublin et al. for a "Telemetry System for Implantable Medical Devices", incorporated herein by reference in its entirety. The antenna may be manufactured as an integral part of implantable device or, that portion of the antenna extending external to the connector block may be manufactured as a separate piece part, coupled to the portion of the antenna within the connector block by means of a standard electrical connector.

BRIEF DESCRIPTION OF THE DRAWINGS

FIG. 2 is a diagram illustrating the interconnection of a first embodiment of an antenna array according to the present invention, including the fixedly mounted antennas and the removably mounted antenna, with RF circuitry and other functional components of the programmer or monitor illustrated in FIG. 1a.

DETAILED DESCRIPTION OF THE DRAWINGS

Figure 1A:
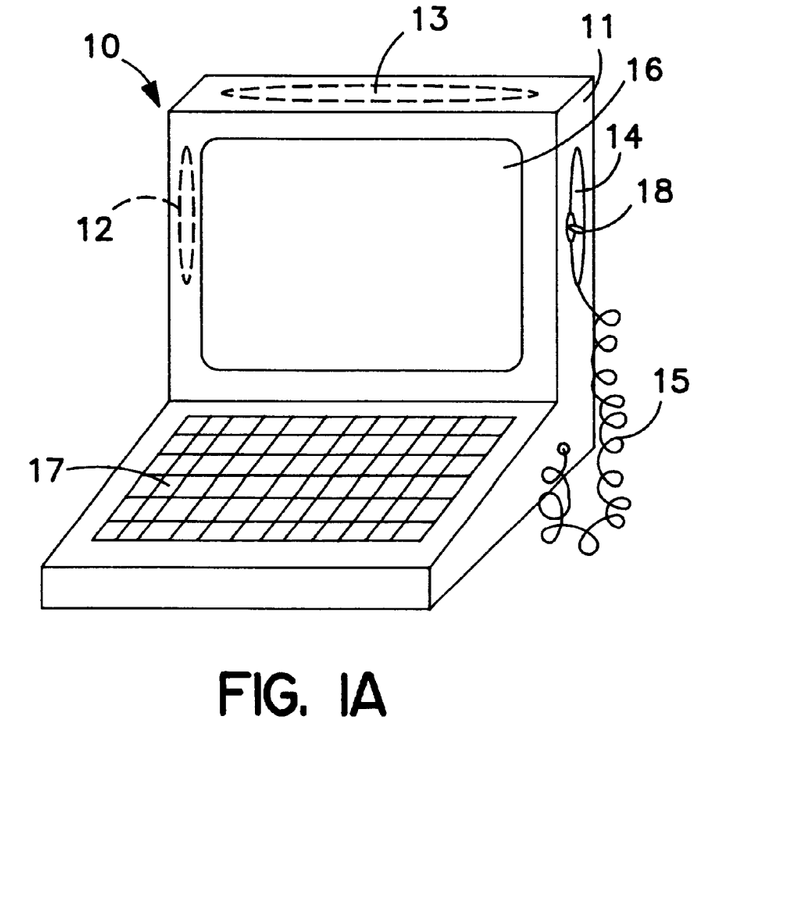
FIG. 1a is a perspective view of a programmer or monitor provided with a first antenna array according to the present invention.

FIG. 1a is a perspective drawing of a programmer or monitor 10 appropriate for use in practicing the present invention. The monitor is provided with a display 16 which may take the form of an LCD display or a CRT and a keyboard 17 which allows the physician to enter commands. The antenna array of the programmer or monitor 10 may include two or three antennas fixedly mounted to the housing, for example corresponding to antennas 12 and 13 as illustrated in broken outline. In this embodiment, the monitor housing is made of non-conductive material and antennas 12 and 13 are located either on the exterior or interior surface of the housing, as is convenient. The third antenna 14 is removably mounted to the exterior of the housing 11 by means of one or more clips 18 and is coupled to the transceiver within the programmer or monitor 10 by means of a coiled cord 15, which is to a length of at least two or three feet and preferably extendible to a greater distance.

Antennas 12 and 13 may be, for example, monopole antennas located relative to one another such that their major axes are generally orthogonal to one another, with removably mounted antenna 14 preferably having its major axis generally orthogonal to antenna 13 when mounted to the housing 11. Similarly, if only one fixedly mounted antenna is employed, e.g. antenna 13, removably mounted antenna 14 would preferably have its major axis generally orthogonal to antenna 13 when mounted to the housing 11. Other types of fixedly mounted antennas may correspond generally to those disclosed in U.S. Pat. No. 5,759,199, issued to Snell et al., U.S. Pat. No. 5,752,976, issued to Duffin et al. U.S. Pat. No. 5,704,351, issued to Mortara et al. or U.S. Pat. No. 4,958,645, issued to Cadell et al, all incorporated herein by reference in their entireties.

Figure 1B:
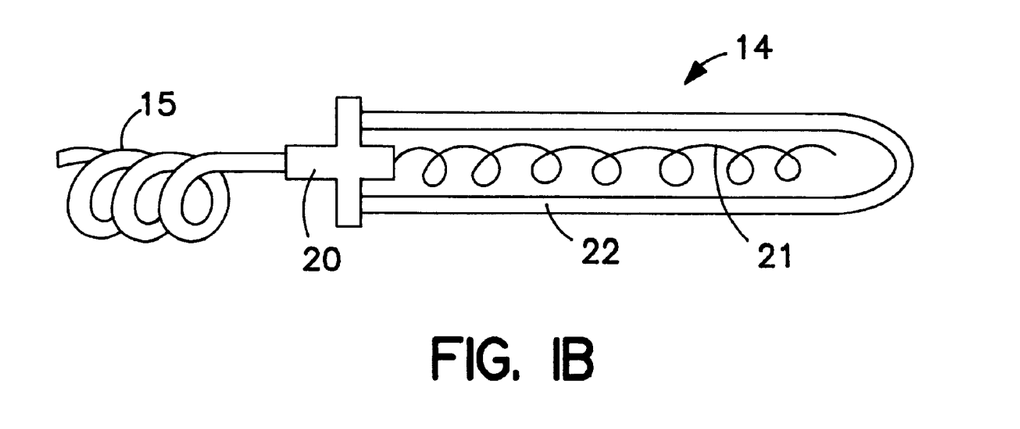
FIG. 1b is a cut-away view of a removably mounted antenna according to the present invention.

FIG. 1b illustrates an exemplary removably mounted antenna appropriate for use in a programmer or monitor as illustrated in FIG. 1a. In this embodiment, antenna 14 takes the form of a tuned monopole, fabricated of a 10 cm long, 1.1 cm diameter 16 turn wire coil 21, connected to coiled cord 15 by connector 29 and covered by a plastic sleeve 22.

Figure 2:
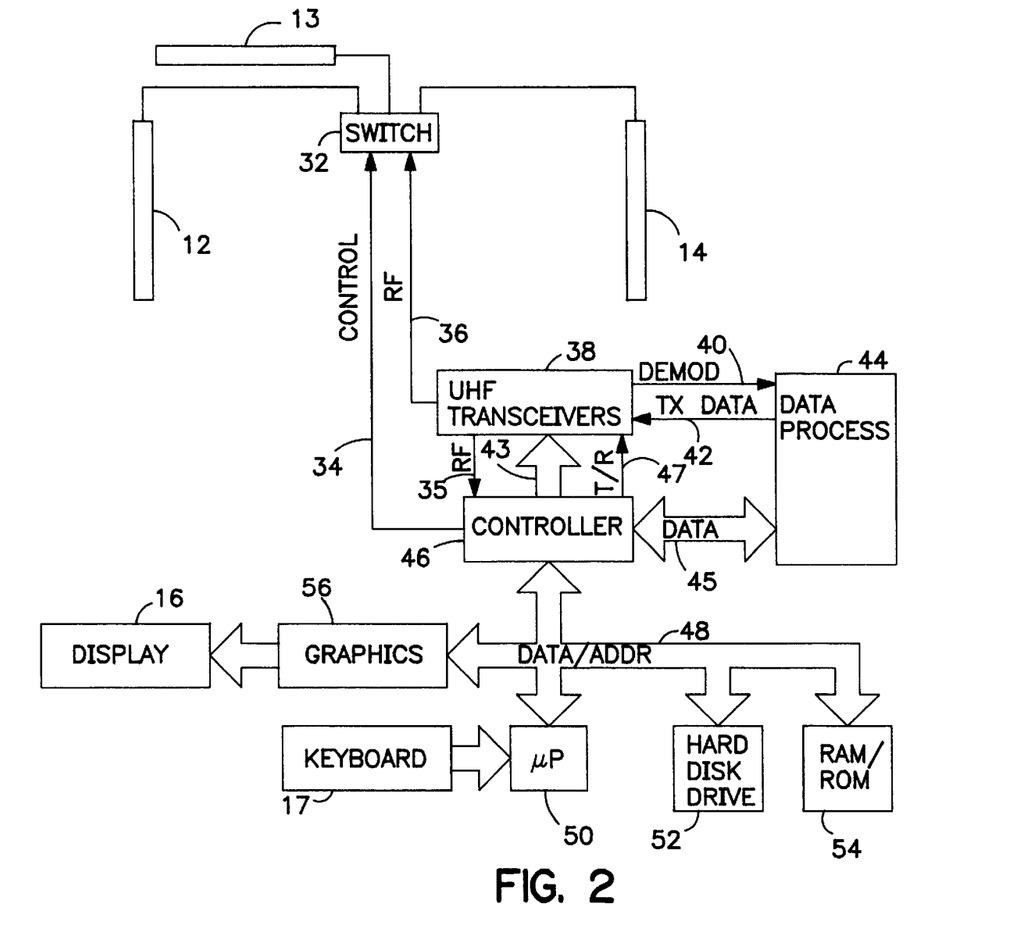

FIG. 2 is a diagram illustrating the interconnection of the antenna array of the programmer or monitor of FIG. 1 a with the RF circuitry and other functional components included therein. The circuitry within the programmer or monitor includes a microprocessor 50 which controls the operation of the device as a function of programming stored in RAM/ROM 54 and/or hard disk drive 52, both of which are coupled to the microprocessor via data/address bus 48. Commands from the physician are provided to the microprocessor via keyboard 17 and/or any additional control buttons (or if the display is touch sensitive from the display as well). Information regarding the operation of the programmer or monitor and information received from the associated implanted device are displayed on display 16, under control of graphics circuitry 56. The graphics circuitry, microprocessor, hard disk drive, RAM/ROM circuitry, keyboard and display may all correspond to corresponding components of personal computers and/or prior art programmers and monitors.

Operation of the telemetry system is controlled by controller circuit 46 which operates under control of microprocessor 50. UHF transceiver 38 is a multi-frequency transceiver, preferably a transceiver capable of operating in a number of frequency bands, in which data is encoded by frequency shift from a defined center frequency. Controller 46 via control bus 43 defines the operational frequency of the transceiver 38, and by means of transmit/receive line. 47 configures the transceiver to either transmit RF signals to the antennas or receive RF signals from the antennas.

Controller 46 also provides the data to be telemetered to the implanted device to data processing circuitry 44 and receives decoded received data from the implanted device from data processing circuit 44, also via data bus 45. Data provided by controller 46 to data processing circuitry 44 is converted therein from parallel to serial format and provided serially to UHF transceiver 38 on TX data line 42. Correspondingly, data received by UHF transceiver 38 is provided in serial format on DEMOD line 40 to data processing circuitry 44, and is converted therein to parallel format and provided to the microprocessor 50 via controller circuitry 46. Controller 46 is also capable of monitoring the amplitude of the signal received by the currently active antenna via RF line 35 from UHF transceiver 38 in order to allow for selection between the two antennas as described above. In operation, during receipt of transmissions from the associated implanted device, the controller 46 may select which of the three antennas is employed as a function of the amplitude of the received RF signal as indicated on RF line 35. Alternatively, the controller may verify the integrity of the data received from data processing circuitry 44 via data line 45, and switch between antennas in the event that the received data has greater than a defined number of errors per transmission. Other measurements of signal quality including signal to noise ratio, bit error rate and the like may also be employed to select between the antennas.

In the event that the programmer needs to also be compatible with implantable devices employing an alternative telemetry format and requiring physical proximity of the programming head and the implanted device, such additional capability may be included in a number of fashions. If the 38 is capable of producing RF signals in the frequency range required for the alternative telemetry format, and the telemetry format does not require a magnetic field, antenna 14 may simply be selected for use by controller 46 and the transceiver 38 employed, for example, to transmit time or interval modulated telemetry transmissions of the types generally described in U.S. Pat. No. 5,350,411, issued to Ryan, et al., U.S. Pat. No. 5,480,415, issued to Cox, et al. or U.S. Pat. No. 4,543,953 issued to Slocum, all incorporated herein by reference in their entireties.

If Antenna 14 is not suitable for transmission of the alternative telemetry format, for example due to the requirement of a magnetic field in conjunction with the RF signal, an additional programming head may instead be coupled to switch 32 by means of a multiple conductor connector, illustrated generally at 15. The programming head, for example corresponding to that in U.S. Pat. No. 5,527,348, issued to Winkler, et al. or U.S. Pat. No. 5,107,833, issued to Barsness, both incorporated herein by reference in their entireties, may instead be selected for use by controller 46 and the transceiver 38 employed, for example, to transmit time or interval modulated telemetry transmissions of the types described in U.S. Pat. No. 5,354,319, issued to Wyborny et al. or U.S. Pat. No. 4,556,063, issued to Thompson et al. or U.S. Pat. No. 5,309,919, issued to Snell et al., all also incorporated herein by reference in their entireties.

As an additional alternative, antenna 14 may take the form of a programming head as described above or otherwise modified to be compatible with the alternative telemetry format. In such an embodiment, antenna 14 may be employed both as a member of the multiple antenna system according to the present invention and as a stand-alone antenna for the alternative telemetry format. As yet an additional alternative, a separate transceiver for the alternative telemetry format might be included and employed either with antenna 14 or an additional antenna or programming head.

Figure 3:
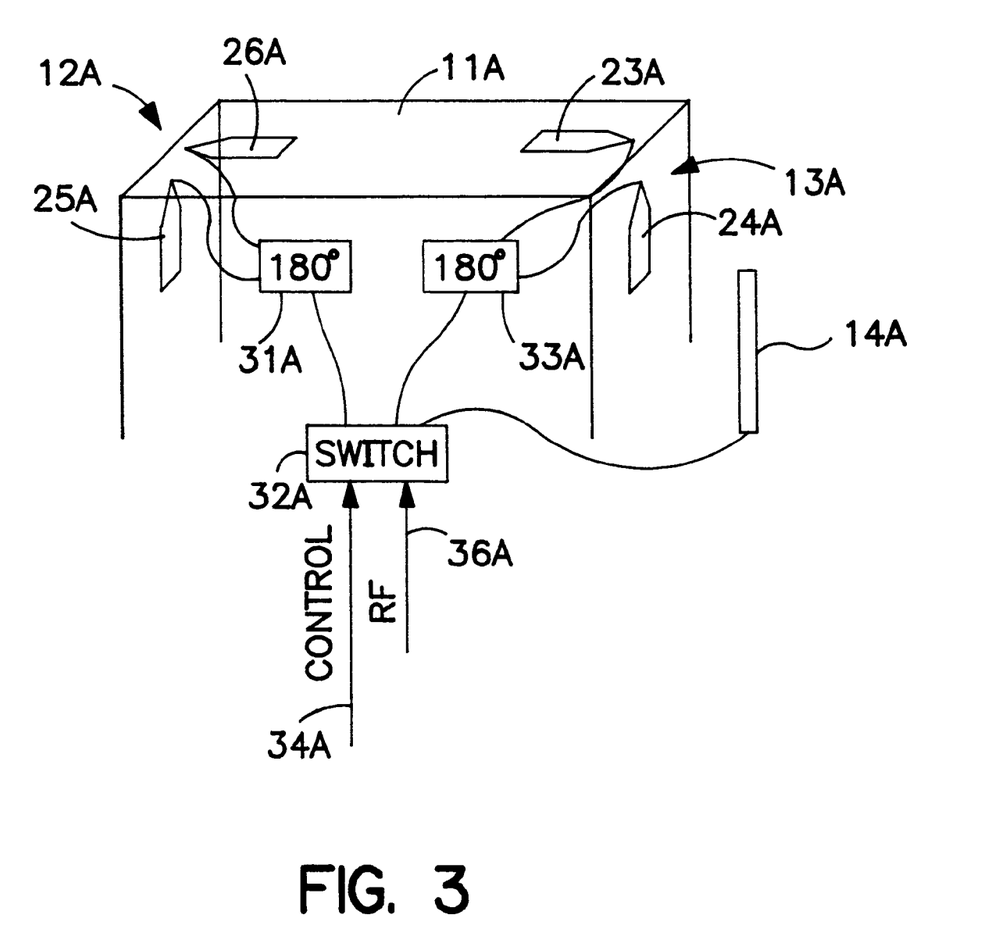
FIG. 3 is a diagram illustrating the interconnection of a second embodiment of an antenna array according to the present invention with the RF circuitry and other functional components of the programmer or monitor as illustrated in FIG. 2.

FIG. 3 is a figure illustrating the interconnection of a first alternative antenna array with corresponding circuitry within the programmer or monitor 10 of FIG 1a. As illustrated, the first antenna 12A includes planar antenna elements 25A and 26A fabricated of metal strips, located adjacent an upper edge of housing 11A, which in this embodiment is fabricated of a non-conductive material. Antenna elements 25 and 26 are coupled to a 180° power splitter/tuned circuit 31A. Similarly, planar antenna elements 23A and 24A of the second antenna 13A located adjacent an opposite upper edge of housing 11A are also coupled to a 180° splitter/tuned circuit 33A. The 180° power splitter/tuned circuits 31A and 33A and removable antenna 14A are coupled to an antenna selector switch 32A corresponding to switch 32 illustrated in FIG. 2 which in turn is coupled to the circuitry within the programmer/monitor via RF line 36A and control line 44A in the same fashion as described in conjunction with FIG. 2.

Figure 4:
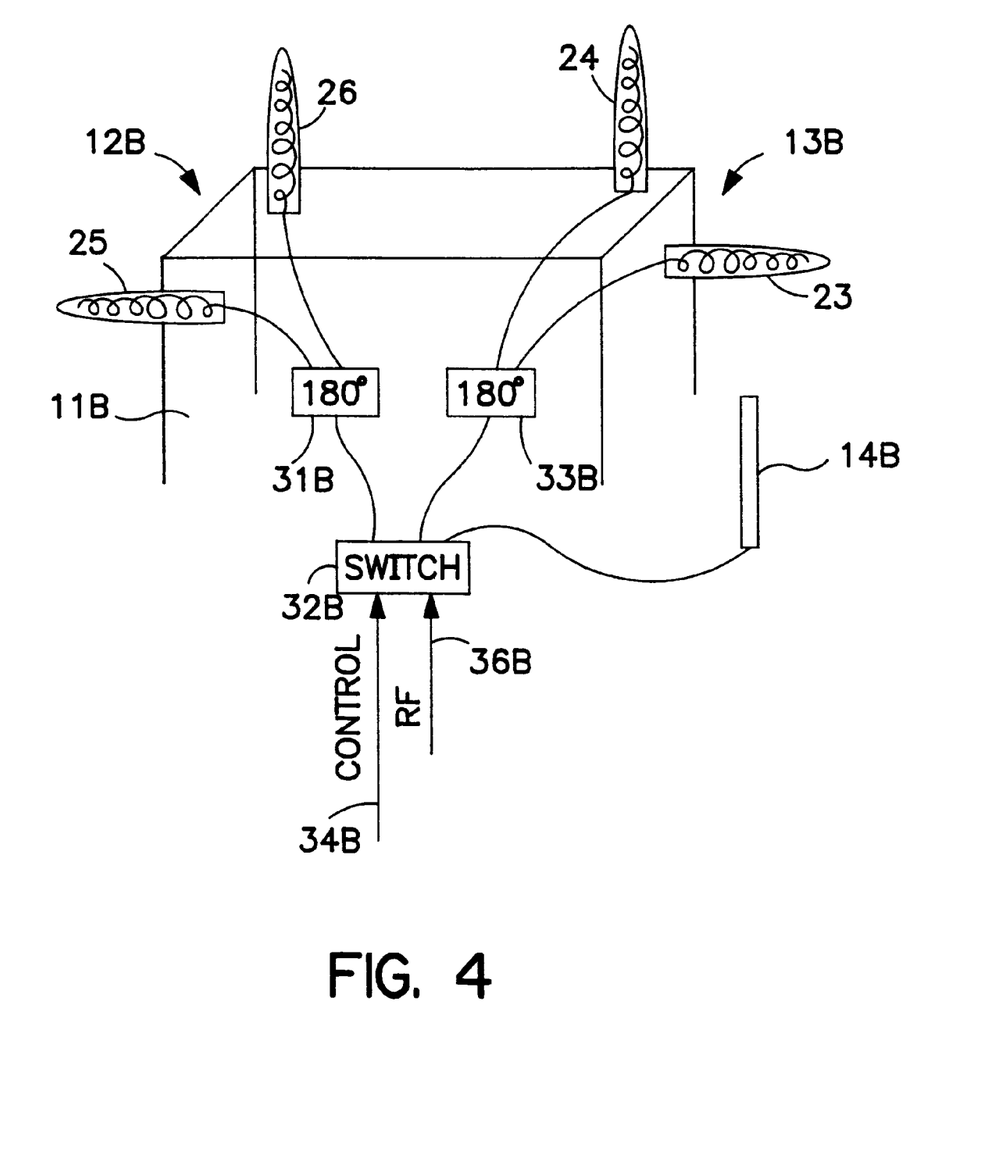
FIG. 4 is a diagram illustrating the interconnection of a third embodiment of an antenna array according to the present invention with the RF circuitry and other functional components of the programmer or monitor as illustrated in FIG. 2.

FIG. 4 is a figure illustrating the interconnection of a second alternative antenna array with corresponding circuitry within the programmer or monitor 10 of FIG 1a. As illustrated, the first antenna 12B includes stub antenna elements 25 and 26, located adjacent an upper edge of housing 11B, which in this embodiment is fabricated of a conductive material. Stub antenna elements 25A and 26A are coupled to a 180° power splitter/tuned circuit 31B which corresponds to the identically labeled circuit in FIG. 3. Similarly, the stub antenna elements 23A and 24A of the second antenna 13B, located adjacent an opposite upper edge of housing 11B are also coupled to a 180° splitter/tuned circuit 33B which also corresponds to the identically numbered component in FIG. 3. The 180° power splitter/tuned circuits 31B and 33B and removable antenna 14B are coupled to an antenna selector switch 32B corresponding to switch 32 illustrated in FIG. 2 which in turn is coupled to the circuitry within the programmer/monitor via RF line 36B and control line 44B in the same fashion as described in conjunction with FIG. 2.

Figure 5:
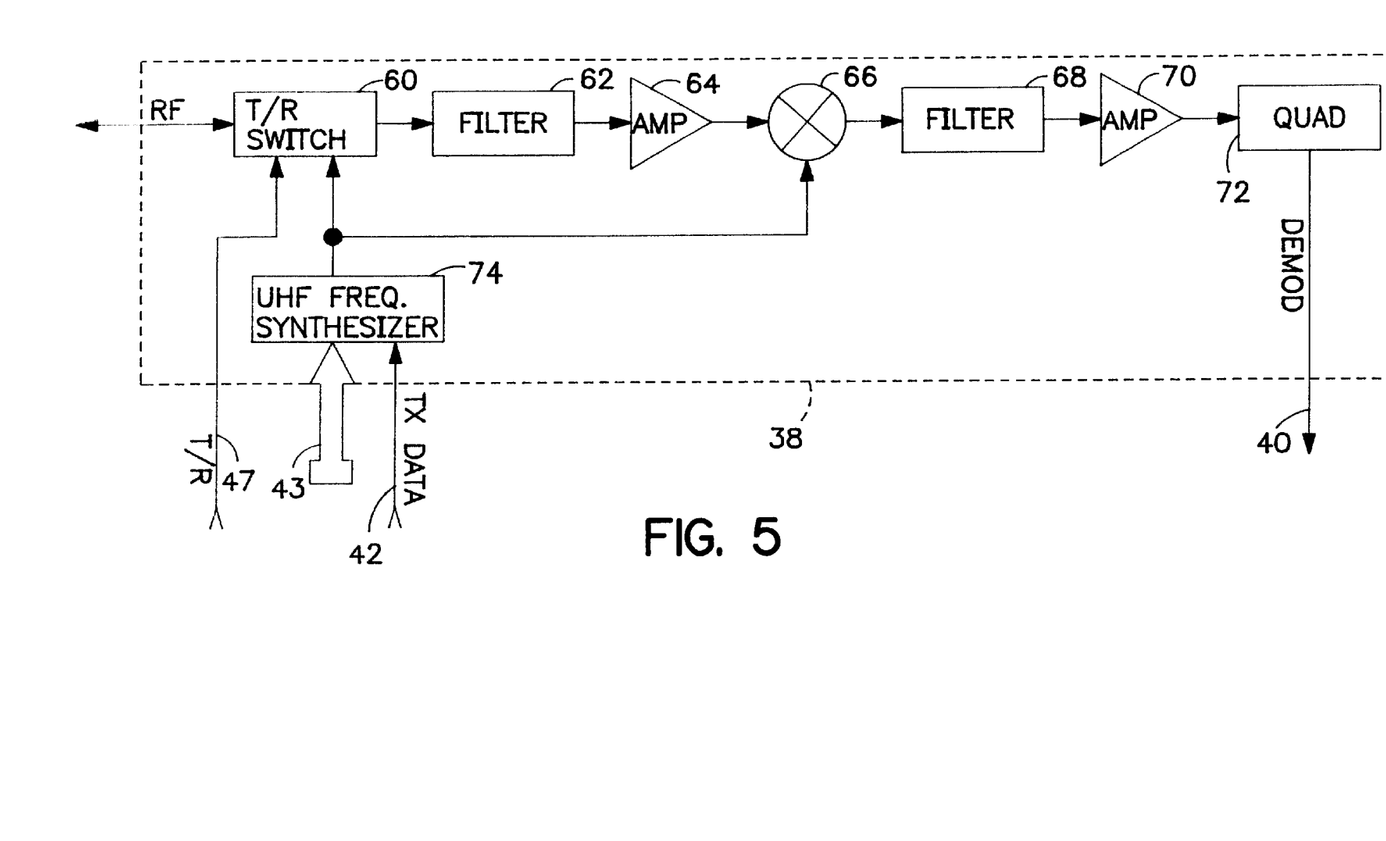
FIG. 5 illustrates an exemplary type of RF transceiver appropriate for use in conjunction with the programmer or monitors of FIGS. 1–4 above and for use in conjunction with the associated implantable devices, according to the present invention.

FIG. 5 is a block functional diagram of one type of a transceiver appropriate for use in conjunction with the present invention. As illustrated, the transceiver is shown as it would be interconnected to the circuitry of the programmer or monitor as illustrated in FIGS. 1a and 2. However, the description of its operation below also may generally apply to the transceiver as employed in the implanted device. Other transceiver types corresponding, for example to transceivers employed in prior art implantable devices and associated programmers may of course be substituted, with corresponding dimensional changes to the antennas as disclosed herein to optimize their performance for the frequencies employed by the transceivers. Examples of alternative transceivers are described in U.S. Pat. No. 5,342,408, issued to DeCoriolis et al., U.S. Pat. No. 5,476,488, issued to Morgan et al., U.S. Pat. No. 5,683,432, issued to Goedeke et al., U.S. Pat. No. 4,365,290, issued to Nelms et al. and U.S. Pat. No. 5,693,076, issued to Kaemmerer or U.S. Pat. No. 5,752,977, issued to Grevious et al., all incorporated herein by reference in their entireties, or as disclosed in any of the above-cited prior patents related to programmers for use with implantable devices.

In particular, the transceiver 38 may be configured to operate employing center frequencies in the vicinity of 400 megaHertz. The receiver includes a UHF frequency synthesizer 74 which operates under control of control bus 43 to define a center frequency and data frequencies spaced above and below the center frequency. A number of center frequencies and associated data frequencies may be defined to provide for multi-channel operation. Control of the transceiver to operate as a transmitter or receiver is accomplished through the transmit/receive control line 47 which causes transmit/receive switch 60 to couple RF line 36 (coupled to the antenna array) to either the frequency synthesizer 74 or to mixer 66 via one or more filtration and amplification stages 62 and 64. While operating as a receiver, the UHF frequency synthesizer applies the center frequency and the signal received from the antenna array to the mixer 66 and thereafter to quadrature detection circuitry 72 via one or more filtration and amplification stages 68 and 70. The demodulated quadrature signal on line 40 is passed through to the data processing circuitry 44 where it is converted from a serial to a parallel format and thereafter provided to the microprocessor 50 via control circuitry 46 and data/address bus 48 (FIG. 3).

During transmission, the transmit/receive switch 68 couples the RF line 36 (in turn coupled to the antenna array) to the output of the UHF frequency synthesizer 74 which outputs a frequency shifted above or below the center frequency as a function of the logic value of the serially applied data on TX data line 42. The associated implanted device correspondingly has a similar UHF transceiver operating in an analogous fashion to receive the RF signals from the programmer or monitor and to transmit RF signals to the programmer/monitor.

Figure 6:
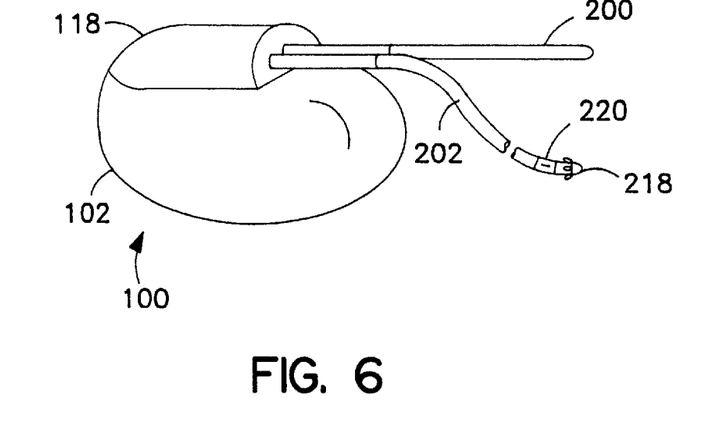
FIG. 6 is a plan view of an implantable device according to the present invention.

FIG. 6 is a perspective view of a first embodiment of an implanted device 100 embodying the present invention. The device includes a hermetic enclosure 102 which includes a battery and electronic circuitry, including an RF transceiver as described above. Mounted to the enclosure 102 is a header or connector block 118 which is preferably fabricated of a plastic such as epoxy. The connector block 118 includes a connector bore which is receives the electrical connector of an associated electrical lead 202, which in this case is a cardiac pacing lead carrying two pacing/sensing electrodes 218 and 220. In some embodiments, such as in the case in which the implantable device is a subcutaneously implantable monitor, no lead may be include. In other embodiments, such as implantable monitors, cardioverters, nerve stimulators or drug pumps, a cardiac monitoring lead, a cardioversion/defibrillation lead, a lead coupled to a physiologic sensor such as an oxygen sensor, pressure sensor, or the like and/or a drug delivery catheter may be provided. The lead is coupled to the internal circuitry within the enclosure 104 by means electrical connectors in connector block 118, each coupled to an associated feedthrough and thereby coupled to the circuitry within enclosure 102. The portion of the antenna 202 external to the connector block may take the form of a wire surrounded by an insulative coating. The wire, for example, may take the form of a stranded or coiled conductor surrounded by silicone rubber insulation 116. The length of wire 114 is chosen to be optimized for use in conjunction with the center frequency of the UHF transceiver within the device 100 and is also coupled to a feedthrough which is in turn coupled to the UHF transceiver within the device 100. The exposed portion of antenna 202 may be permanently attached to the connector block 118 or may be removably attached in the same fashion as lead 202.

Figure 7:
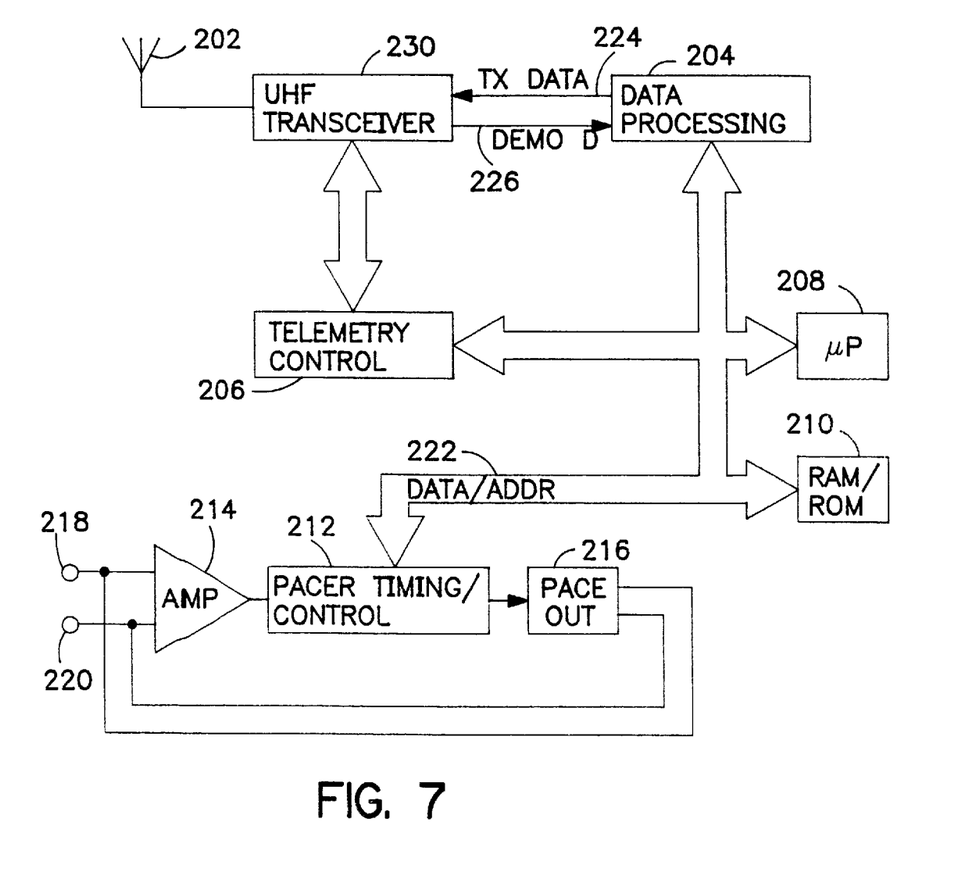
FIG. 7 is a functional block diagram of an implantable device according to the present invention.

FIG. 7 is block functional diagram of an implantable device as illustrated in FIG. 6, appropriate for use in practicing the present invention. In this case, the device takes the form of an implantable cardiac pacemaker, which operates under control of microprocessor 208 under control of programming stored in RAM/ROM circuitry 210. Basic timing and operational functions of the pacemaker are provided by pacer/timing control circuitry 212, which defines the various escape intervals, pulse widths, sensing intervals and the like associated with operation of a cardiac pacemaker. Selection of intervals in operative modes is accomplished by microprocessor 208 via data/address bus 222. As illustrated, the device is provided with an input amplifier 214 which senses cardiac depolarizations via electrodes 218 and 220. For example, electrodes 218 and 220 may be located on an electrical lead associated with the device and inserted into a connector receptacle of the header coupled to the device enclosure, as illustrated in FIGS. 6 through 9, above. An output pulse generator 216 is provided for delivering cardiac pacing pulses to electrodes 218 and 220 according to any of the standard cardiac pacing modes. The illustrated embodiment of the implantable device as a cardiac pacemaker is purely exemplary, and it should be understood that the implantable device may of course take the form of an implantable nerve stimulator, implantable heart monitor, implantable drug pump or any other implantable electronic device which employs a telemetry system to communicate between the implanted device and an associated external programmer or monitor.

The telemetry circuitry of the implantable device corresponds generally to that discussed above in conjunction with FIG. 3 in the context of the associated external programmer or monitor. The antenna 200 is coupled to a UHF transceiver 230 which may correspond to the UHF transceiver 38 illustrated in FIGS. 2 and 5 described above. Alternatively, the transceiver 38 may take the form of a zero IF or direct conversion transceiver of the general type described in U.S. Pat. No. 4,523,324 issued to Marshall et al., U.S. Pat. No. 4,618,967 issued to Vance et al and U.S. Pat. No. 4,580,101 issued to Lax et al., all incorporated herein by reference in their entireties. The transceiver in such embodiments may correspond generally to zero IF direct conversion FSK paging receivers intended to operate in the UHF band.

Like the circuitry within the programmer, operation of the transceiver is controlled via control bus 228 by telemetry control circuitry 206 which may correspond generally to control circuitry 46 of FIG. 3. Demodulated data from UHF transceiver 202 is provided via DEMOD line 226 to data processing circuitry 204 which converts the data from serial format to parallel format and provides it to microprocessor 208 via data/address bus 222. Data to be transmitted is converted from parallel format to serial format and provided to the transceiver via TX data line 224, in a fashion analogous to that discussed above in conjunction with FIG. 3 in the context of the external programmer or monitor.

While in the embodiment illustrated the removable antenna is coupled to the transceiver of the programmer or monitor by means of a cord, it is within the scope of the invention to employ alternative mechanisms for coupling the removable antenna to the transceiver while the antenna is at a distance from the programmer or monitor. For example, the mechanism for removably mounting the antenna to the housing may include an electrical connector, which would be disconnected when the antenna is removed from the housing. In this embodiment, the programmer and antenna may be interconnected when at a distance from one another by means of an infra-red, ultrasonic or other wireless communication link, for example a communication link as disclosed in U.S. Pat. No. 5,759,199, issued to Snell et al., U.S. Pat. No. 5,383,915, issued to Adams, both incorporated herein by reference in their entireties.

In conjunction with the above specification, I claim:

1. An external device for use in communication with an implantable medical device, comprising:

a device housing;

a device controller, mounted within the device housing;

a spatial diversity antenna array mounted to the device housing;

an RF transceiver operating at defined frequency, located within the device housing, coupled to the antenna array;

means for encoding signals to be transmitted to the implantable device, coupled to an input of the transceiver;

means for decoding signals received from the implantable device, coupled to an output of the transceiver; and means for displaying demodulated signal received from the implanted device, mounted to the device housing;

wherein the antenna array comprises a first antenna permanently mounted to the device housing and a second antenna removably mounted to the device housing and locatable at a distance from the housing and means for coupling the removable antenna to the RF transceiver while the removable antenna is located at a distance from the device housing; and wherein the device controller includes means for selecting which of the two antennas in the antenna array is coupled to the transceiver.

2. A device according to claim 1 wherein the means for coupling the removable antenna to the RF transceiver while the removable antenna is located at a distance from the device housing comprises a cord extendible to a distance of at least several feet.

3. A device according to claim 1 wherein the transceiver is a UHF transceiver.

4. A system comprising an external device and an associated implantable device, wherein the external device comprises:

an external device housing;

a device controller, mounted within the external device housing;

an antenna array mounted to the external device housing;

a first RF transceiver operating at defined frequency, located within the external device housing, coupled to the antenna array;

means for encoding signals to be transmitted to the implantable device, coupled to an input of the first transceiver;

means for decoding signals received from the implantable device, coupled to an output of the first transceiver; and means for displaying demodulated signal received from the implanted device, mounted to the external device housing;

wherein the antenna array comprises a first antenna permanently mounted to the device housing and a second antenna removably mounted to the device housing and locatable at a distance from the housing and means for coupling the removable antenna to the first transceiver while the removable antenna is located at a distance from the device housing; and wherein the device controller includes means for selecting which of the two antennas in the antenna array is coupled to the first transceiver; and wherein the implantable device comprises:

a hermetic housing;

a second transceiver mounted within the hermetic housing; and an antenna coupled to the second transceiver.

5. A system according to claim 4 wherein the transceivers arc UHF transceivers.

6. A device according to claim 4 wherein the means for coupling the removable antenna to the first transceiver while the removable antenna is located at a distance from the device housing comprises a cord extendible to a distance of at least several feet.

* * * * *

UNITED STATES PATENT AND TRADEMARK OFFICE
CERTIFICATE OF CORRECTION

PATENT NO. : 6,167,312
DATED : December 26, 2000
INVENTOR(S) : Steven D. Goedeke It is certified that error appears in the above-identified patent and that said Letters Patent is hereby corrected as shown below:

Column 8, claim 1,
Line 14, "to be transmitted" should read -- transmittable --
Line 17, "received" should read -- receivable --
Line 19, "received" should read -- receivable --
Line 20, "implanted" should read -- implantable --

Column 8, claim 4,
Line 49, " to be transmitted" should read -- transmittable --
Line 52, "received" should read -- receivable --
Line 54, "received" should read -- receivable --
Line 55, "implanted" should read -- implantable --.

Signed and Sealed this

Fifth Day of March, 2002

Attest:

JAMES E. ROGAN
*Attesting Officer*      *Director of the United States Patent and Trademark Office*